United States Patent
Brendel et al.

(10) Patent No.: US 6,301,962 B1
(45) Date of Patent: Oct. 16, 2001

(54) WEIGHT COMPENSATING ARRANGEMENT FOR A DISPLACEABLE EXAMINATION COMPONENT OF A MEDICAL APPARATUS

(75) Inventors: Frank Brendel, Coswig; Roland Reuther, Dresden, both of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/382,454

(22) Filed: Aug. 25, 1999

(30) Foreign Application Priority Data

Sep. 9, 1998 (DE) ............................... 198 41 200

(51) Int. Cl.[7] .............................. G01M 1/00; A47B 71/00
(52) U.S. Cl. .................................... 73/480; 5/600
(58) Field of Search ................... 73/480; 5/600, 5/601, 607, 608, 610

(56) References Cited

U.S. PATENT DOCUMENTS

| | | |
|---|---|---|
| 4,021,715 | 5/1977 | Von Hacht et al. ............ 318/628 |
| 5,014,969 * | 5/1991 | Schaefer ....................... 5/600 |
| 5,029,826 * | 7/1991 | Schaefer ....................... 5/600 |
| 5,477,575 * | 12/1995 | Lehne et al. ..................... 5/601 |

FOREIGN PATENT DOCUMENTS

| | | |
|---|---|---|
| 1 728 886 | 8/1956 | (DE) . |
| 2 104 509 | 7/1973 | (DE) . |
| 40 41 294 | 7/1991 | (DE) . |

* cited by examiner

Primary Examiner—Richard A. Moller
(74) Attorney, Agent, or Firm—Schiff Hardin & Waite

(57) ABSTRACT

Weight compensating arrangement for a displaceable examination component of a medical system has a lever arrangement and a controllable adjusting device which acts on a first lever arm in order to exert a compensating force for the weight of the examination component which act on the other lever arm. This produces an optimal weight compensation and a reduced mass of the medical device compared to conventional arrangements.

13 Claims, 3 Drawing Sheets

WEIGHT COMPENSATING ARRANGEMENT FOR A DISPLACEABLE EXAMINATION COMPONENT OF A MEDICAL APPARATUS

BACKGROUND OF THE INVENTION

1. Field of the Invention

The present invention is directed to an arrangement for compensating the weight of a displaceable component, such as a component used in the examination of a subject in a medical examination apparatus.

2. Description of the Prior Art

This type of weight compensating arrangement is employed in an X-ray examination apparatus with a target device which can be rotated around an axis together with an allocated mounting plate. The target device can also be displaceable along the mounting plate. This type of target device has a large dead weight and so requires a weight compensating arrangement, so that it is not displaced by gravity given a displacement of the mounting plate from the horizontal into the vertical, for example. Such target devices have a mass of approximately 200 to 350 kg. A displacement therefore requires the application of a large physical force. For this reason, in these types of tilting-table examination devices, the counterweight of the target device is compensated with an equally large counterweight, and a motorized support is provided for the displacement. The motorized drive of the support, which is switched on and off in the handle of the target device, for example, designed to overcome only the frictional forces of the system, which is weight-balanced in all device positions, so that the manual force required of the operator for displacing the target device is very small. It is a disadvantage that the total weight of the radiography device is increased by the counterweight, and effective collision protection requires a high outlay due to the large masses to be moved, because of their mass inertia. Solutions are known for reducing the mass of the counterweight wherein the counterweight is fixedly arranged at a long lever arm of a lever system with two arms, a spring also engaging the lever arm, and the force of the weight of the target device acts on at the shorter lever arm. This enables a mass reduction of the counterweight in proportion to the length of the lever arm. Counterweight balancing according to this principle is taught in German Utility Model 17 28 886, for example. A disadvantage of this apparatus is that the weight balancing is optimal only for a specific orientation of the tilting-table examination device at which the displacement forces for the target device are also minimal. In device positions which deviate from this, i.e. given a pivoted position which deviates from this optimal position, there is not an exact weight balancing, because the weight of the target device, which depends on the sine of the tilt angle, is balanced only for one position, namely this optional position. Although the mass can be appreciably reduced in this way, problems also arise in the collision protection due to the mass inertia, and in addition, measures are required in order to suppress the control loop oscillation of the motorized drive of the support, particularly at the beginning of a displacement, such oscillation being caused particularly by the spring. Given a constant drive power of the motorized drive of the support and an uncontrolled displacement speed, the problem arises that the displacement speed of the target device unintentionally depends on the tilt angle of the tilting-table examination device.

German OS 40 41 294 teaches a weight balancing arrangement which likewise has a weight-loaded lever arrangement for compensating the weight of the target device. One lever arm is weight-loaded, while the weight of the target device acts on the other lever arm. In this device as well, the weight of the target device is only compensated in a specific position (+90°). With this arrangement, it is possible to reduce the counterweight mass depending on the lever relations. For collision protection, force sensors are allocated to the lever arm, which generate a signal for deactivating the motorized drive of the support dependent on the excursion of the lever arm from the neutral position when the target device approaches an obstacle. This principle is unusable for real technical use in an examination device, however, because an excursion of the lever arm can occur given the tilting of the target device by the changing weight acting on the lever arrangement, even though the target device does not encounter an obstacle. Measures that involve great outlay are necessary to prevent the occurrence of an unintended deactivation of the motorized drive of the support.

German AS 21 04 509 teaches a support arrangement for the displacement of a target device in which the acting displacement force is detected in a handle of the target device according to magnitude and direction by high-resolution force sensors. These force sensors are biased with the weight of the total mass of the target device. Given a weight of 3500 N, great outlay is required to evaluate a displacement force that is usually in a range between 10 and 50 N, and to execute the corresponding control of the motorized drive of the support in a reproducible manner.

German PS 24 01 853 teaches a method wherein a force sensor signal is combined with a differentiating tachometer signal for purposes of achieving a control value for advancement of the target device, in order to achieve the lowest possible weight required for the displacement and to achieve a linear relation between the size of the displacement force acting at the target device and the torque of the support drive. The generated tachometer signal has a disturbing amplitude ripple which is amplified by differentiation of the signal. A smoothing of the signal by an integrator is not possible because the dynamic behavior of the support drive is very unfavorably affected by this. The cost of this known arrangement is increased by the necessity of providing a compensation winding for preventing the lever from reacting to the non-linearity of the tachometer signal. It is likewise unfavorable that the support drive is used for compensating the weight of the target device, for which purpose energy must be continuously supplied thereto.

SUMMARY OF THE INVENTION

An object of the present invention is to provide a weight compensating arrangement for a displaceable examination component of a medical system wherein an optimal weight compensation is always obtained, regardless of the apparatus orientation, with an optimally small weight increase of the medical system and given an optimally simple and thus economic structure.

The above object is achieved in accordance with the principles of the present invention in a weight compensating arrangement for a displaceable examination component, such as in a medical examination system, having a lever arrangement and a controllable adjusting assembly which engages a first lever arm of the lever arrangement in order to exert a compensating force thereon for the weight of the component, which acts on the other lever arm of the lever arrangement.

It is an advantage of the invention that the weight compensating arrangement has a lever mechanism and a controllable adjusting device acting on a first lever arm of the support for producing a compensation force for the weight, which acts on the other lever arm. It is thus possible to forgo a counterweight for balancing the weight, since the controllable adjusting device produces this counter-force. This type of controllable adjusting device is considerably lighter than the necessary counterweight, so that the negative influence of the masses to be moved is appreciable reduced. Such a controllable adjusting device, moreover can be implemented in a structurally simple manner; the corresponding drive parts are standard parts and are thus not expensive.

The lever arrangement can have a first long arm and a second short arm, and the controllable adjusting device can engage the long arm, and the weight can engage the short arm, so that, depending on the lever ratio, only relatively little energy must be supplied to the controllable adjusting device in order to compensate the weight.

In a further embodiment, a force sensor is allocated to the lever arrangement and a control means is allocated to the controllable adjusting device, and the signal of the force sensor is fed to the control unit for actuating adjusting device to set the required compensation weight, so that the weight is always compensated, regardless of the pivoting of the examination means.

The same advantage is achieved by having the controllable adjusting device engage the lever arrangement via at least one elastic element and providing an excursion detector at the lever arrangement, the excursion detector generating a signal, depending on the excursion of the lever arrangement, which is fed to the control unit. On the basis of this signal an actuation of the controllable adjusting device to compensate the excursion of the lever arrangement can be effected. Force sensors with corresponding evaluation electronics need not be used. In particular, optical or inductive distance sensors or sensors which operate with sound or high frequency can be used, which generate an analog or digital signal.

Particularly advantageously, an electromechanical device can be used as the controllable adjusting device. Such a device is compact in structure and requires only a small control outlay.

The signal of the force sensor or of the excursion means also can be used for actuating a displacement assembly for the examination apparatus, which produces a supported displacement in the direction of the force acting on the examination apparatus at the operating handle, for example. Depending on the range of force acting on the force sensor or dependent on a first excursion range, the displacement assembly can be actuated and, if the first range of force or the first excursion range is/are exceeded, the controllable adjusting device can be actuated as well.

By allocating an acceleration sensor to the lever arrangement, an interruption of the control of the displacement assembly can occur depending on the signal of this sensor, so that collision protection is easily obtained.

DESCRIPTION OF THE PREFERRED EMBODIMENTS

Figure 1:
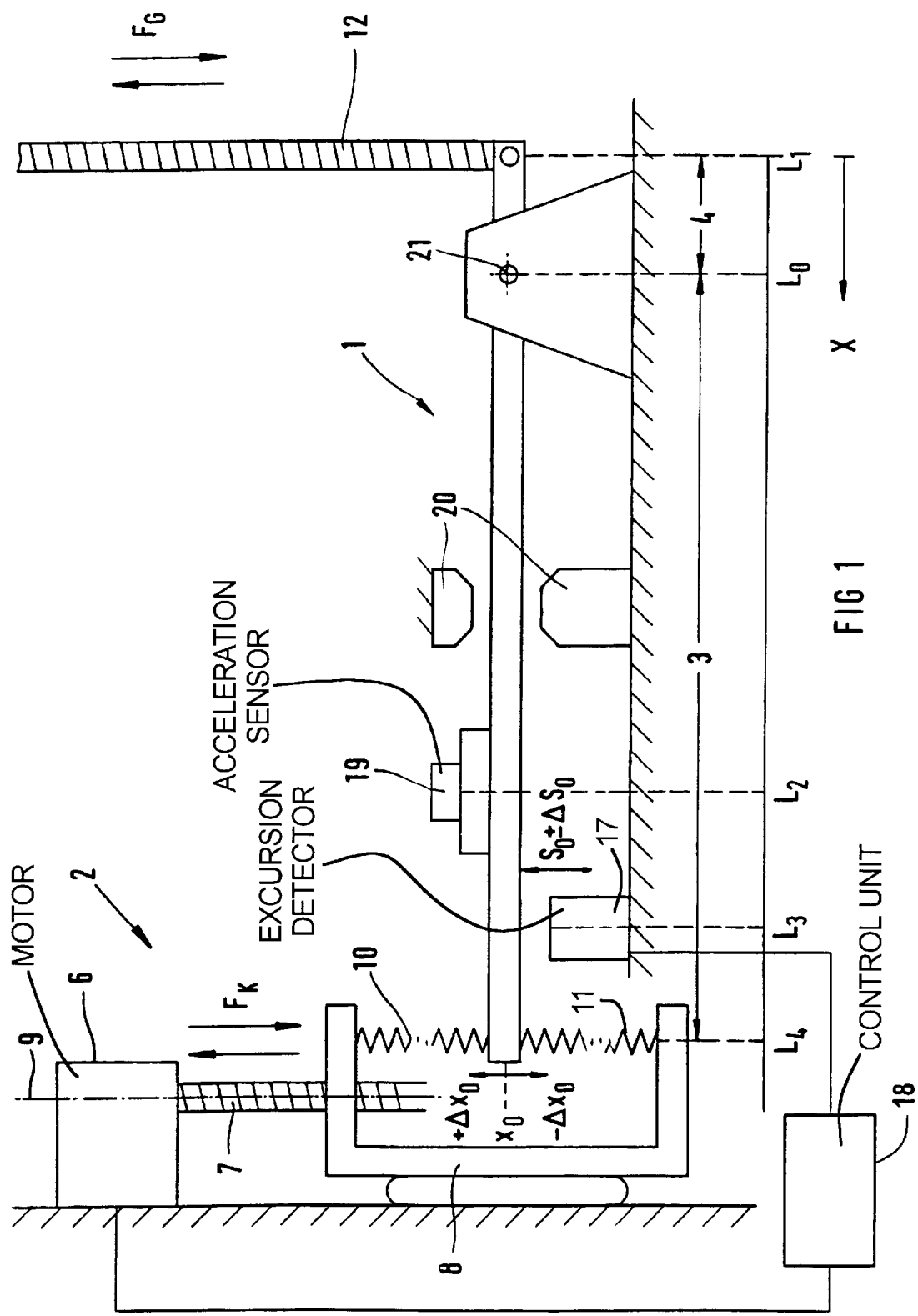
FIG. 1 shows an exemplary embodiment of an inventive weight compensating arrangement.

The weight compensating arrangement illustrated in the figures in an exemplary embodiment is for an examination component 5 of a medical system. The weight compensating arrangement has a lever arrangement 1 and a controllable adjusting device 2 which acts on a first lever arm 3 in order to exert a compensating force $F_k$ for the weight $F_G$, which acts on the other lever arm 4. The controllable adjusting device 2, which is preferably an electromagnetic device, has a motor 6, with a transmission, if necessary, which engages the first lever arm 3 via a link, which can be a spindle, for example, preferably a self-locking spindle. To this end, as is illustrated in FIG. 1, the spindle 7 can engage one short leg of a U-shaped mounting block 8 which acts as a spindle nut, and which can be displaced along its longitudinal axis 9 by the motor 6. In the exemplary embodiment, the U-shaped mounting block 8 engages the first lever arm 3 via a resilient element 10 that is arranged at this short leg. A resilient displacement is thus possible for the lever arrangement 1. As also shown in the exemplary embodiment, an additional resilient element 11 engages the first lever arm 3 and at the other short leg of the U-shaped mounting block 8, which is remote from the spindle 7. The first lever arm 3 is thus mounted between the short legs of the U-shaped mounting block 8 by the resilient elements 10, 11. The resilient elements 10, 11 preferably are made of a helical spring material. The spring force of the resilient element 10, in particular, is adjusted such that it is at least equal to the weight $F_G$ of the examination component 5. The use of two resilient elements 10, 11 is necessary when, in a medical device illustrated in FIG. 2, for example, a tilting of the bearing mechanism 15 is possible from the horizontal into a head or foot position, for instance by a tilt angle in the range from −20° to +90°.

It is understood within the context of the invention that the U-shaped mounting block 8 acting as a spindle nut can be replaced by a simple plate-like link that can be displaced at the spindle 7, and that preferably engages the first lever arm 3 via the resilient element 10. This version is somewhat more economical; however, the resilient element 10 is loaded by pulling and pushing.

In a still more economical development, the spindle 7 can be displaced along its longitudinal axis 9 and engage the first lever arm 3 directly, via the resilient element 10, with its end that is remote from the motor 6. Such a version is sufficient when the bearing mechanism 15 can be displaced from the horizontal only in one direction, for example.

Figure 2:
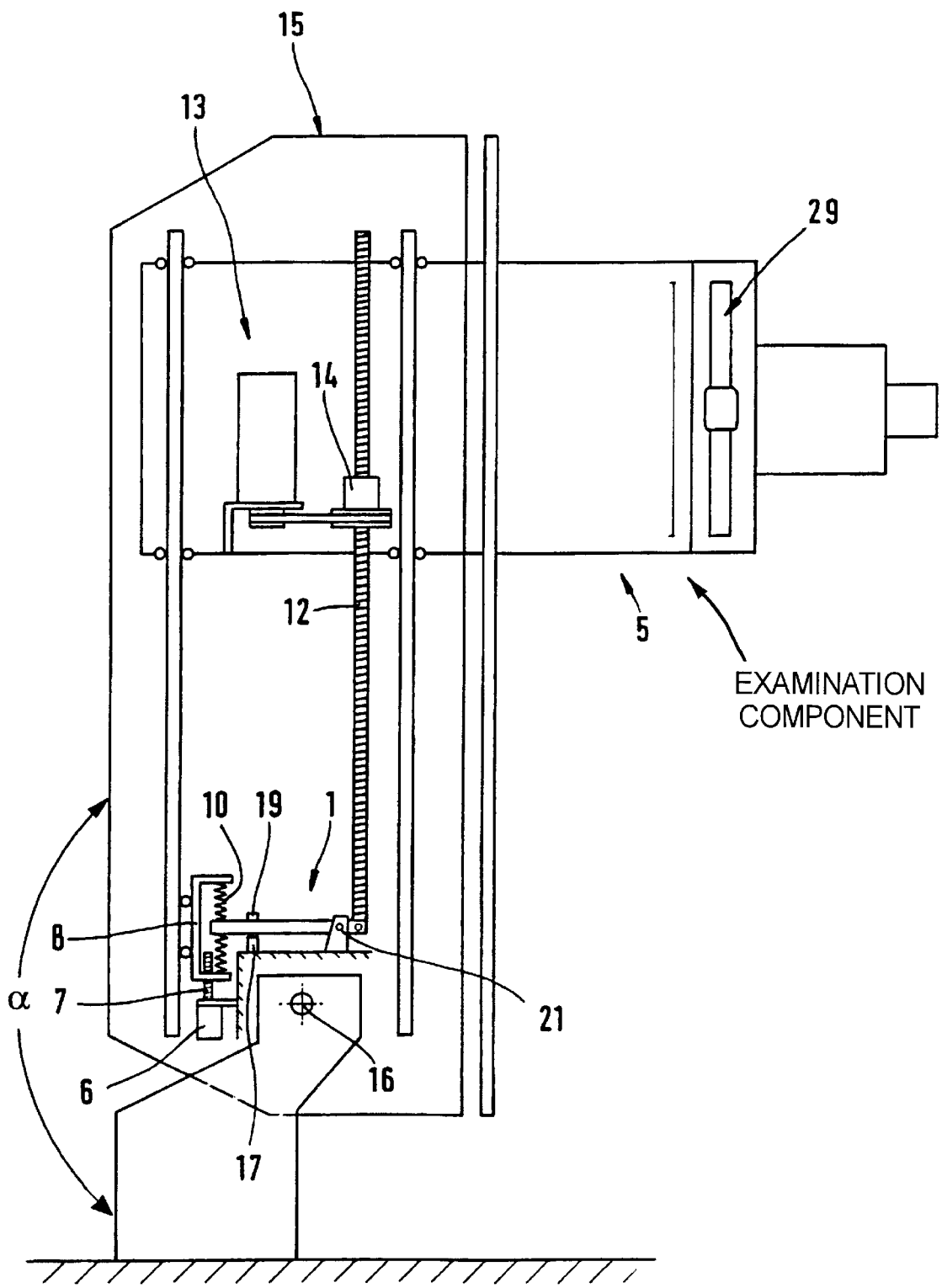
FIG. 2 shows an exemplary embodiment of a medical device with a weight compensating arrangement according to FIG. 1.

At the other short lever arm 4 of the lever arrangement 1, an additional spindle 12 is mounted, which preferably is constructed as a ball spindle and is in connection with the examination component 5 for transferring the weight $F_G$ into the lever arrangement 1, as shown in FIG. 2. For displacing the examination component 5, a displacement assembly 13 is provided which enables a displacement of the examination component 5 along the additional spindle 12. To this end, the displacement assembly 13, which is preferably electromechanically operated is connected with an element, such as a spindle nut, which engages the additional spindle 12. The desired displacement of the examination component 5 can be effected by the influence of a force at the operating handle 29. Under the influence of the force, direction-dependent contacts can be actuated. Given the closing of one of the contacts, for instance, an output signal x1 is fed to the excursion detection unit 17 as control signal for the displacement assembly 13. If none of the contacts are closed, for example, the weight compensation is activated via the controllable adjusting device 2.

Figure 3:
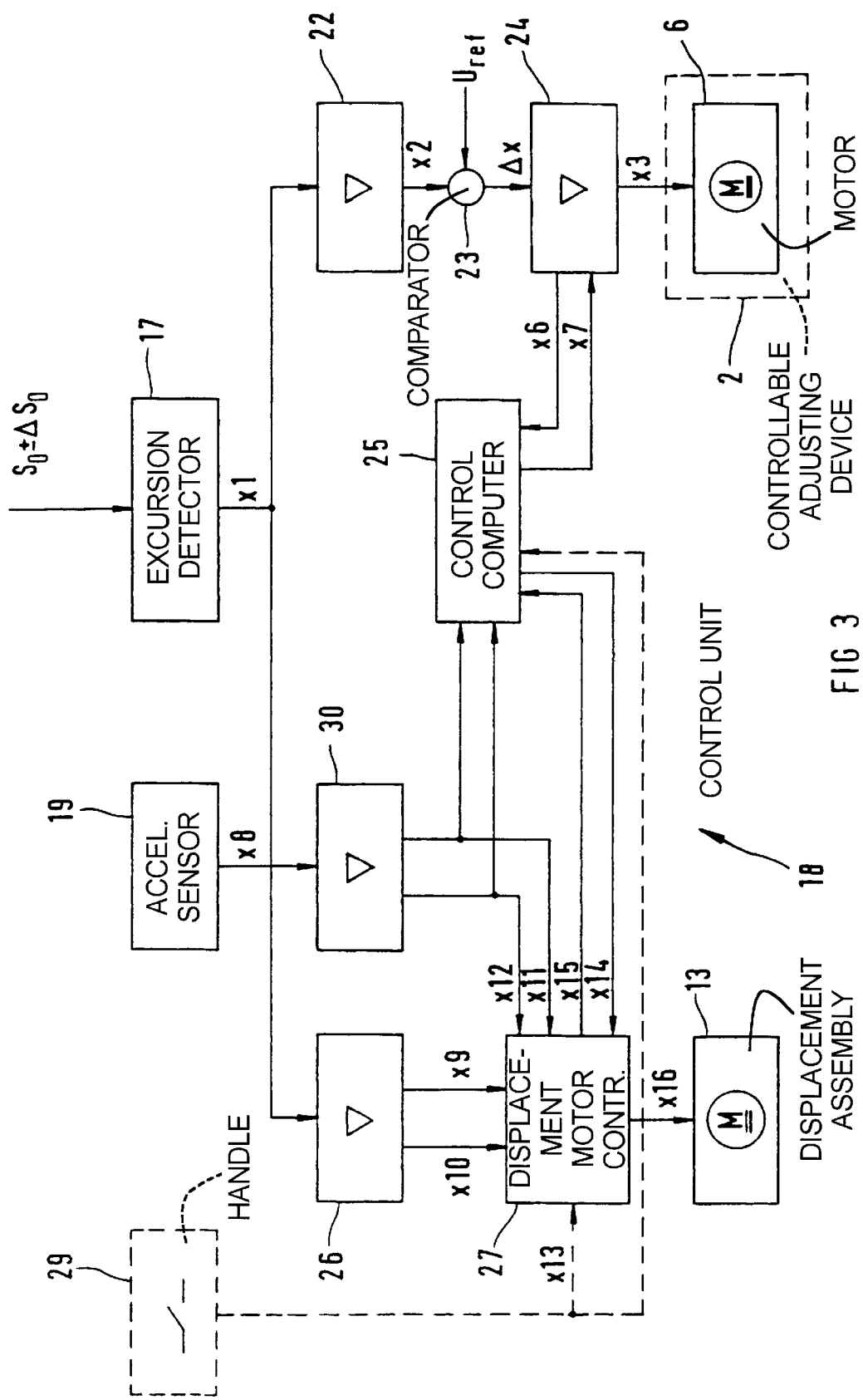
FIG. 3 shows a control circuit of the weight compensating arrangement according to FIG. 1.

As shown in FIG. 2 the examination component 5 has a bearing mechanism 15 for an examination subject, which can be pivoted around an axis 16 from the vertical direction (+90°) illustrated in FIG. 2 through a horizontal orientation into a tilt (−20°). The examination component 5 is, in the exemplary embodiment, a target device which can be displaced along the bearing mechanism 15 via the displacement assembly 13. In the vertical orientation of the bearing mechanism 15, the greatest weight $F_G$ acts on the lever arrangement 1 from the target device, so that the adjusting device 2 must be actuated for the purpose of exerting the necessary compensation force $F_K$. Given the swivelling of the bearing mechanism 15 into the horizontal, the weight $F_G$ is reduced, so that a corresponding actuating of the adjustment device 2, to reduce the compensation force $F_K$, must occur. An excursion detector 17 is provided for this purpose, which detects a weight-caused excursion of the lever arrangement 1, particularly of the first lever arm 3. This excursion detector 17 can detect the excursion of the lever arrangement 1 optically, inductively, with ultrasound, with an angle position indicator that is allocated to the lever arrangement 1, or with a distance sensor that operates with high frequency. The signal of the excursion detector 17 is fed to a control unit 18 that is detailed in FIG. 3, which actuates the adjustment device 2 to generate the required compensation force $F_K$, so as to level (balance) the lever arrangement 1. An acceleration sensor which generates a signal whenever the target device contacts an obstacle also can be allocated to the lever arrangement 1, for example. In this case, a blocking (disabling) of the displacement assembly 13 occurs, or the target device is displaced in the opposite direction.

An excursion limiter 20 is also allocated to the lever arrangement 1, which limits excessive excursions of the lever arms 3,4 when, for example, a spiral spring breaks or the weight $F_G$ exceeds a predetermined value.

A more detailed description of the invention follows. Controlling of the weight compensation occurs with the two-armed lever arrangement 1 which is mounted in a fulcrum 21. Via the additional spindle 12, which is constructed as a ball spindle, the weight $F_G$, which depends on the sine of the tilt angle of the bearing mechanism 15, is introduced at the location $L_1$. This weight $F_G$ acts at the location $L_1$ on the other lever arm 4 of a length $L_0$ to $L_1$ and is automatically counterbalanced with a controllable compensation force $F_K$ at the first lever arm 3 of a length $L_0-L_4$. It has proven advantageous for the ratio of the lever arms 3,4 to be in the range from 1:5 to 1:20, preferably >1:10. As a measurement term for this counterbalancing, the excursion $(S_0 \pm \Delta S_0)$ for the first long lever arm 3 at the location $L_3$ is determined. This excursion detector 17 is a sensor with a high sensitivity of 1.6 V/mm, for example, and delivers a linear output signal x1 depending on the excursion of the first lever arm 3. Force sensors could also be used here, though these are expensive in view of the required evaluation electronics. The introduction of the compensation force $F_K$ occurs at the location $L_4$. In the counterbalanced state, the product of lever arm length $L_0-L_4$ and $F_K$ equals the product of lever arm length $L_0-L_1$ and $F_G$. The output signal x1 of the excursion detector 17 is amplified in an amplifier 22 and is compared in a comparator 23 to a reference voltage $U_{ref}$ which represents the set point of the counterbalancing control loop and which defines a distance $S_0$ between the excursion detector 17 and the first lever arm 3 at the location $L_3$. A control deviation $\Delta x$ controls a motor controller 24 of the motor 6 of the controllable adjusting device 2. The output signal x3 (which is preferably a pulse-width modulation (PWM) signal) of the motor controller 24 controls the DC motor 6, which drives the spindle 7 (preferably a self-locking trapezoidal spindle) so that the resilient elements 10,11 are biased via the U-shaped mounting block 8 so that the resulting force at the location $L_4$ puts the first lever arm 3 into the counterbalanced state $S_0$. The self-locking trapezoidal spindle 7 mechanically "stores" the compensation force $F_K$, even if a voltage is not fed to the motor controller 24. This counterbalancing control loop automatically controls all changes of the weight $F_G$ which act at the location L1. The proper counterbalancing is indicated to a control computer 25 with the signal x6.

To effect a displacement of the examination component 5, an operating handle 29 is provided which acts on direction control contacts. When the operating handle 29 is displaced into a specific position, a direction control contact is activated, and an output signal x1 is fed to the excursion detector 17 as a control reference for the displacement assembly 13. If a direction control contact is not activated, then the weight compensating means is activated.

A servocontrol loop for the target device's longitudinal displacement is described below. The output signal x1 of the excursion detector 17 can also serve for purposes of detecting a force acting at the examination means 5 for purposes of its displacement with reference to its direction in that, depending on the force, an excursion of the lever arrangement 1 and thus a modification of the output signal x1 occurs. In the exemplary embodiment, a deactivation signal x7 is delivered by the control computer 25 to the motor controller 24, and an activation signal x14 is delivered to a displacement motor controller 27 for the electromechanical displacement assembly 13. The output signal x1 of the excursion detector 17 is fed to a displacement amplifier 26, so that an analog voltage from 0 to +10V corresponds to a rotation rate variation of the electromechanical displacement assembly 13 of from 0 to 2500 rpm. The force direction signal x9 is derived from the output signal x1 of the excursion detector 17 and is fed as a motor controller signal x16 to the electromechanical displacement assembly 13 via the displacement motor controller 27 as a PWM voltage (if the displacement assembly 13 has a DC motor). Preferably, a BLC motor is used, to which the phase voltages and the commutation signals are fed. On the basis of this servocontrol loop, a displacement of the examination component 5 occurs dependent on the direction of the acting force and the speed, this displacement being supported by the electromechanical displacement assembly 13, so that to an operator it feels as if the examination component 5 can be moved practically without force. Alternatively, and in a more economical version, a force direction signal also can be derived via a force acting on the operating handle 29 of the examination component 5, if at least one force sensor is allocated to the handle 29. The signal of the force sensor is referenced x13 in FIG. 3 and is fed both to the control computer 25 and to the displacement motor controller 27 as a release signal.

As explained above, an acceleration sensor 19 is allocated to the lever arrangement 1, whose acceleration signal x8, which corresponds to the acceleration, is fed to an acceleration signal amplifier 30, where it is amplified and fed to the control computer 25 and to the displacement motor controller 27 as an acceleration quantity signal x11, which corresponds to the acceleration with respect to magnitude, and an acceleration direction signal x12. If the acceleration quantity signal x11 and the acceleration direction signal x12 exceed predefined values, then the activation signal x14 is interrupted via the control computer 25 and is conducted to the displacement motor controller 27, which stops the actuation of the electromechanical control assembly 13, or which actuates the control assembly to produce an actuation in a direction opposite to the direction of displacement of the examination component 5.

In the framework of the invention, sensors can likewise be allocated to the excursion limiter 20, these sensors generating a signal whenever the motion of the first lever arm 3 is stopped by the excursion limiter 20. This signal is then fed to the control computer 25, which generates an error signal which is brought to the operator's attention by indication at a display means, for example.

Although modifications and changes may be suggested by those skilled in the art, it is the intention of the inventors to embody within the patent warranted hereon all changes and modifications as reasonably and properly come within the scope of their contribution to the art.

We claim as our invention:

1. An arrangement for compensating for a weight of a displaceable component, comprising:

a lever arrangement having a first lever arm and a second lever arm, a weight of a displaceable component acting on said second lever arm; and a controllable adjusting device engaging said first lever arm for producing a force which compensates for said weight acting at said second lever arm.

2. An arrangement as claimed in claim 1 wherein said first lever arm is longer than said second lever arm.

3. A weight compensating arrangement as claimed in claim 1 further comprising a force sensor allocated to said lever arrangement for producing a signal representing said weight acting on said lever arrangement, and wherein said controllable adjusting device includes a control unit, supplied with said signal from said force sensor, said control unit actuating said controllable adjusting device to produce said compensating force dependent on said signal from said force sensor.

4. An arrangement as claimed in claim 1 wherein said controllable adjusting device comprises at least one resilient element connecting said first lever arm to said controllable adjusting device, and an excursion detector allocated to said lever arrangement, said excursion detector emitting a signal dependent on an excursion of said lever arrangement, and said controllable adjusting device including an excursion control unit, supplied with said signal from said excursion detector, said excursion control unit actuating said controllable adjusting device dependent on said signal from said excursion detector to compensate excursion of said lever arrangement.

5. An arrangement as claimed in claim 1 wherein said controllable adjusting device comprises an electromechanically controllable adjusting device.

6. An arrangement as claimed in claim 1 further comprising a displacement assembly connected to said component for displacing said component to assist in displacement of said component in a direction of said weight on said component.

7. An arrangement as claimed in claim 6 wherein said displacement assembly comprises an electromechanical displacement assembly, and further comprising an acceleration sensor allocated to said lever arrangement which emits a signal dependent on acceleration of said lever arrangement, said signal being supplied to said electromechanical displacement assembly and said electromechanical displacement assembly controlling displacement of said component dependent on said signal.

8. An arrangement as claimed in claim 1 wherein said controllable adjusting device comprises at least one resilient element connecting said first lever arm to said controllable adjusting device, and an excursion detector allocated to said lever arrangement, said excursion detector emitting a signal dependent on an excursion of said lever arrangement, and said controllable adjusting device including an excursion control unit, supplied with said signal from said excursion detector, said excursion control unit actuating said controllable adjusting device dependent on said signal from said excursion detector to compensate excursion of said lever arrangement, and further comprising an electromechanical displacement assembly connected to said component, for assisting in displacing said component in a direction of a force acting on said component, said electromechanical displacement assembly including a displacement control unit, supplied with said signal from said excursion detector, and wherein said electromechanical displacement assembly is actuated and said controllable adjusting device is passive in an absence of said signal from said excursion detector, and wherein said electromechanical displacement assembly is passive and said controllable adjusting assembly is actuated upon a presence of said signal from said excursion detector.

9. An arrangement as claimed in claim 1 wherein said examination component comprises a target device having a support mechanism with an axle around which said target device is rotatable.

10. An arrangement as claimed in claim 1 further comprising an electromechanical displacement assembly connected to said examination component for assisting in displacement of said examination component in a direction of a force acting on said examination component, said electromechanical displacement assembly including a rotatable spindle engaging said examination component and rotated by said electromechanical displacement assembly to displace said examination component.

11. An arrangement as claimed in claim 10 wherein said spindle comprises a ball spindle.

12. An arrangement as claimed in claim 1 further comprising an excursion limiter allocated to said lever arrangement for limiting movement of said lever arrangement.

13. An arrangement as claimed in claim 12 further comprising means connected to said excursion limiter for generating an error signal if a predetermined movement of said lever arrangement is exceeded.

* * * * *